(12) United States Patent
deSouza et al.

(10) Patent No.: US 6,832,108 B2
(45) Date of Patent: Dec. 14, 2004

(54) ENDOVAGINAL MRI RECEIVER COIL

(75) Inventors: Nandita M. deSouza, London (GB); David J. Gilderdale, Bovey Tracey (GB)

(73) Assignee: Koninklijke Philips Electronics, N.V., Eindhoven (NL)

( * ) Notice: Subject to any disclaimer, the term of this patent is extended or adjusted under 35 U.S.C. 154(b) by 506 days.

(21) Appl. No.: 09/837,950

(22) Filed: Apr. 19, 2001

(65) Prior Publication Data

US 2002/0156370 A1 Oct. 24, 2002

(51) Int. Cl.$^7$ .................................................. A61B 5/05
(52) U.S. Cl. ...................................... 600/423; 600/422
(58) Field of Search .............................. 600/423, 422, 600/410, 407, 412; 324/307, 306, 309

(56) References Cited

U.S. PATENT DOCUMENTS

| | | | |
|---|---|---|---|
| 5,050,607 A | 9/1991 | Bradley et al. | 128/653 A |
| 5,348,010 A | 9/1994 | Schnall et al. | 128/653.2 |
| 5,355,087 A | 10/1994 | Claiborne et al. | 324/322 |
| 5,451,232 A | 9/1995 | Rhinehart et al. | 606/192 |
| 5,476,095 A | 12/1995 | Schnall et al. | 128/653.2 |
| 5,921,926 A * | 7/1999 | Rolland et al. | 600/407 |
| 6,051,974 A | 4/2000 | Reisker et al. | 324/318 |
| 6,141,577 A * | 10/2000 | Rolland et al. | 600/407 |
| 6,501,980 B1 * | 12/2002 | Carlon et al. | 600/423 |
| 6,549,800 B1 * | 4/2003 | Atalar et al. | 600/423 |

OTHER PUBLICATIONS

N.M. deSouza, et al. "Magnetic resonance imaging of the Anal Sphincter Using an Internal Coil." *Magnetic Resonance Quarterly*, vol. 11, No. 1. © 1995 Raven Press, Ltd., New York, NY. pp 45–46.

N.M. deSouza, et al. "High–Resolution MR Imaging of the Female Anal Sphincter Using a dedicated Endoanal Coil: Normal Features and appearances Following Obstetric Trauma." Hammersmith Hospital, London.

* cited by examiner

*Primary Examiner*—Daniel Robinson
(74) *Attorney, Agent, or Firm*—Fay, Sharpe, Fagan, Minnich & McKee, LLP

(57) ABSTRACT

An MRI apparatus includes a local endovaginal probe (30) for receiving magnetic resonance in a study of the endopelvic fascia surrounding the female urethra. The probe (30) includes a shaft portion (62) an insert portion (60), the insert portion to be inserted into the vaginal cavity of a female subject. The insert portion (60), in order to have maximum efficiency in imaging the endopelvic fascia, is designed to specific dimensions to achieve the optimum balance between image quality and patient comfort. In an imaging sequence, a main magnet assembly (12) produces a main magnetic field through an imaging region (14). A whole-body RF coil (26) excites and manipulates magnetic resonance in the vicinity of the vaginal cavity. The probe (30) detects the magnetic resonance, which is received and demodulated. The received magnetic resonance is then reconstructed into an image representation of the tissue surrounding the vaginal cavity of the subject.

21 Claims, 3 Drawing Sheets

12
ENDOVAGINAL MRI RECEIVER COIL

BACKGROUND OF THE INVENTION

The present invention relates to the diagnostic imaging arts. It has particular application in conjunction with imaging vaginal anatomy and will be described with particular reference thereto. It will be appreciated, however, that the invention is also applicable to the imaging of other portions of the female pelvic region, and is not limited to the aforementioned application.

Urinary incontinence is a common problem affecting women of all age groups. It is a source of embarrassment and anxiety for many women, especially those of advancing years. As longevity increases, urinary incontinence becomes more of a problem because women can develop this problem with age. As a result, researchers have undertaken the task of investigating the underlying causes of urinary incontinence.

Magnetic resonance imaging has allowed significant advances in the areas of understanding of urinary incontinence in females, however, there is still much that is unknown.

Previous methods of investigating urinary stress incontinence have utilized external coils and relate to the description of the pelvic floor muscles, ligaments, and zonal anatomy of the urethra. However, these methods were insufficient for viewing an endopelvic fascia, that is, tissues between the vaginal muscularis and adjacent organs and the pelvic wall.

Endocavitary coils such as the coils of U.S. Pat. No. 6,051,974 to Reisker, et al. have been utilized. However, this type of coil was designed to be inserted into the anus of male patients to examine the prostate, rather than the area around the vagina in female patients. As a result, tissues around the vagina were distorted and images were not useful in a study of the vagina.

The present invention provides a new and improved method and apparatus which overcomes the above-referenced problems and others.

SUMMARY OF THE INVENTION

In accordance with one aspect of the present invention, a magnetic resonance apparatus is provided. A main magnet assembly produces a substantially uniform main magnetic field in an imaging region. Magnetic resonance is excited and manipulated in selected dipoles of a subject in the imaging region by an RF coil assembly. An RF vaginal receive coil assembly receives magnetic resonance signals from tissues surrounding the vaginal cavity of the subject. A reconstruction processor reconstructs received magnetic resonance signals into an image representation.

In accordance with another aspect of the present invention, a magnetic resonance method is provided. A main magnetic field is induced in an imaging region, a subject being located within the imaging region. A vaginal fascia receive coil is inserted into a vaginal cavity of the subject, the coil having an insert portion and a shaft portion. Magnetic resonance is excited and manipulated in selected dipoles adjacent to the vaginal cavity. The resonance signals are received, demodulated, and reconstructed into an image representation.

In accordance with another aspect of the present invention, a magnetic resonance receive coil assembly is provided. The assembly includes a coil loop, tuning and matching circuitry, and a coil housing for encasing the coil loop and the tuning and matching circuitry.

One advantage of the present invention is that it presents a reusable MRI endocavitary probe.

Another advantage resides in high resolution image representations of the endopelvic fascia.

Another advantage is that it provides images with less distortion of the imaging volume.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

Figure 1:
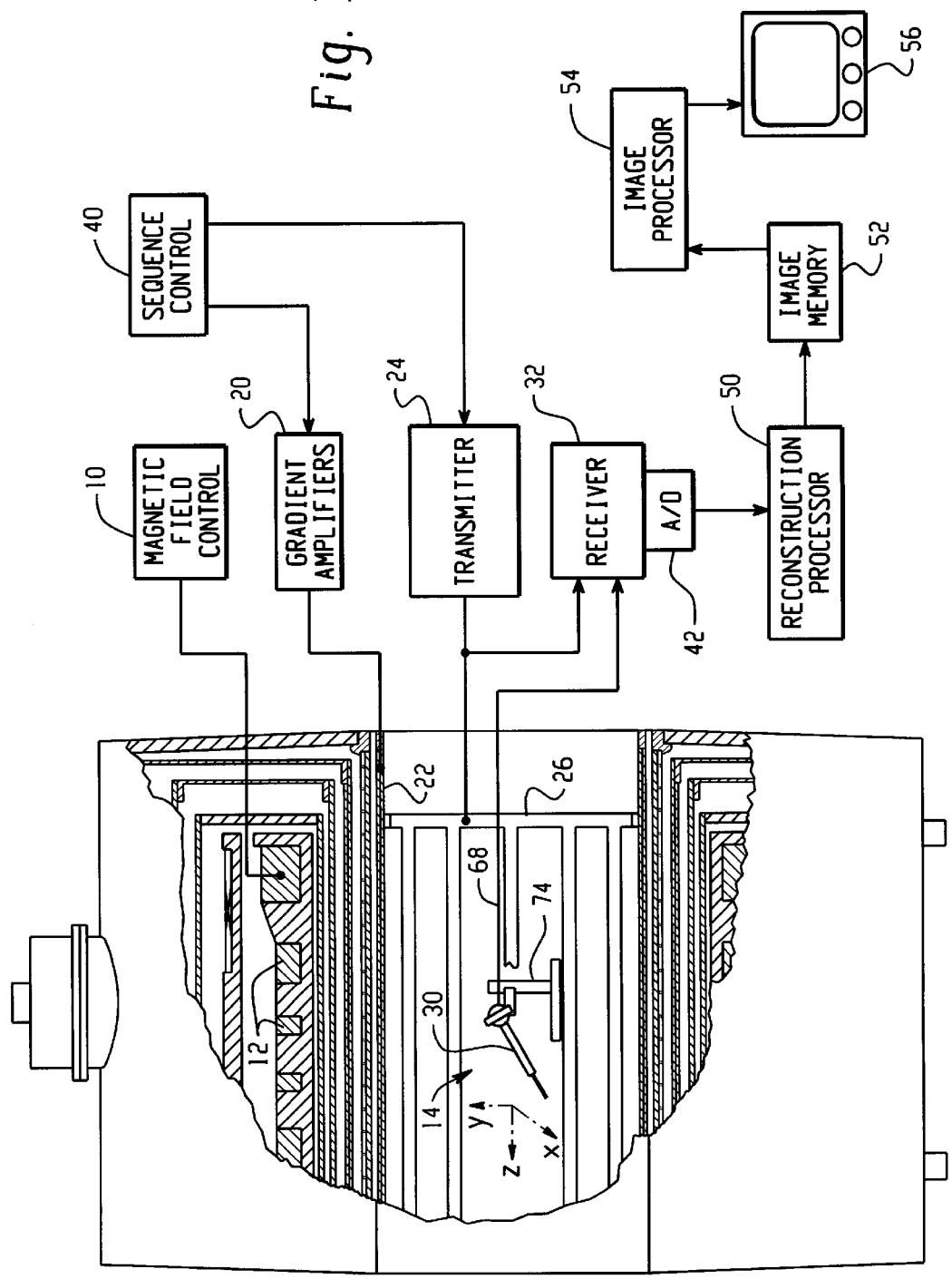
FIG. 1 is a diagrammatic illustration of a magnetic resonance apparatus including a reusable vaginal cavity probe in accordance with the present invention.

With reference to FIG. 1, a main magnetic field control 10 controls superconducting or resistive magnets 12 such that a substantially uniform, temporally constant main magnetic field is created along a z axis through an examination region 14. A magnetic resonance generation and manipulation system applies a series of radio frequency (RF) and magnetic field gradient pulses to invert or excite magnetic spins, induce magnetic resonance, refocus magnetic resonance, manipulate magnetic resonance, spatially and otherwise encode the magnetic resonance, to saturate spin, and the like to generate magnetic resonance imaging and spectroscopy sequences. More specifically, gradient pulse amplifiers 20 apply current pulses to selected ones or pairs of whole-body gradient coils 22 to create magnetic field gradients along x, y and z-axes of the examination region 14. A digital radio frequency transmitter 24 transmits radio frequency pulses or pulse packets to a whole-body RF coil 26 to transmit RF pulses into the examination region. A typical radio frequency pulse is composed of a packet of immediately contiguous pulse segments of short duration which taken together with each other and any applied gradients achieve a selected magnetic resonance manipulation. The RF pulses are used to saturate, excite resonance, invert magnetization, refocus resonance, or manipulate resonance in selected portions of the examination region. For whole-body applications, the resonance signals are commonly picked up by the whole-body RF coil 26.

For generating images of limited regions of the subject, local coils are commonly placed contiguous to the selected region. A receive-only local endovaginal radio frequency coil probe 30 receives resonance signals introduced by body-coil RF transmissions. The resultant radio frequency signals are picked up by the endovaginal probe 30, the whole-body RF coil 26, or other specialized RF coils and demodulated by a receiver 32, preferably including a preamplifier (not illustrated).

A sequence control circuit 40 controls the gradient pulse amplifiers 20 and the transmitter 24 to generate any of a plurality of multiple echo sequences such as echo planar imaging, echo volume imaging, gradient and spin echo imaging, fast spin echo imaging, and the like. For the selected sequence, the receiver 32, preferably a digital receiver, generates a plurality of digital data lines in rapid succession following each RF excitation pulse. optionally an analog-to-digital converter 42 converts the demodulated data to form the digital data lines. The digital data lines are reconstructed into an image representation by a reconstruction processor 50 which applies a Fourier transform or other appropriate reconstruction algorithm. The image may represent a planar slice through the patient, an array of parallel planar slices, a three-dimensional volume, or the like. The image is then stored in an image memory 52 where it may be accessed by a video processor 54 that converts slices, projections, or other portions of the image representation into appropriate format for a display, such as a video monitor 56 which provides a human-readable display of the resultant image.

Although a bore type magnet is illustrated, it is to be appreciated that open or vertical field magnets are equally applicable.

Figure 2:
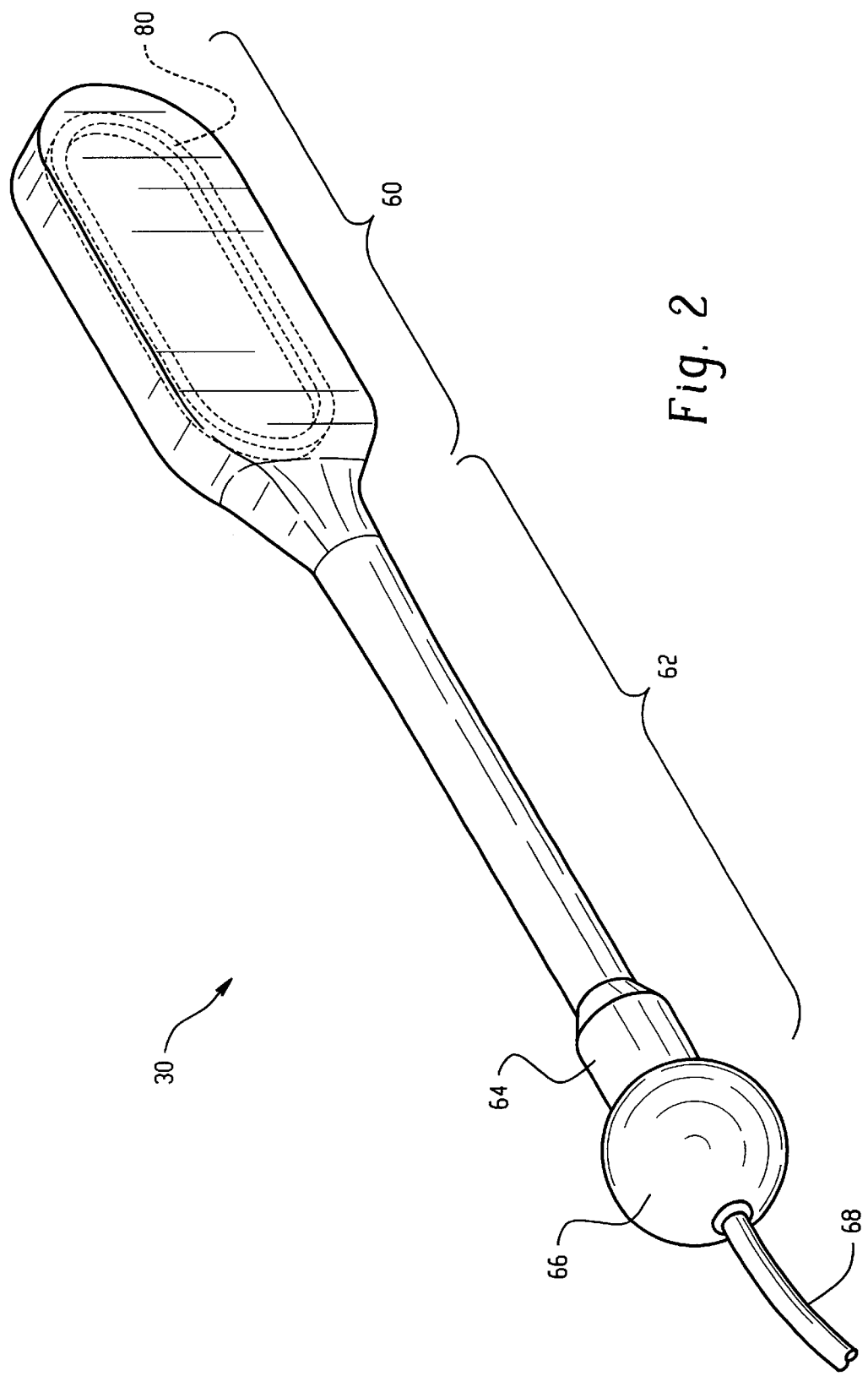
FIG. 2 is a perspective view of the vaginal cavity probe, in accordance with the present invention.

With reference to FIG. 2, the endovaginal probe 30 includes an insert portion 60 and a shaft portion 62 which are inserted into a vaginal cavity of a subject being examined contiguous to the endopelvic fascia. The proximity of the coil to the region of interest provides for a relatively high signal-to-noise ratio. Both the insert portion 60 and the shaft portion 62 are preferably constructed seamlessly of a medical grade plastic, such as Delrin™, or epoxy. Eliminating seams eliminates shelter for microorganisms, making sterilization a more facile task. The Delrin™ is appropriately flame retardant and is specifically intended for limited exposure to mucus membrane or blood barrier contact. The shaft portion 62 is telescopically connected to an enlarged portion 64 of the shaft portion 62. The enlarged portion 64 grants extra support for an interface of the shaft portion 62 with an over-molded form 66.

The over-molded form 66 seals an open proximate end of the shaft 62. Preferably, the over-molded form 66 is constructed of PVC plastic. An RF cable 68 extends from outside the RF coil assembly through the over-molded form 66. A portion of the over-molded form 66 is embedded in circumferential grooves and flats formed on the outer surface of an enlarged portion 64 of the shaft 62 to provide, a tight mechanical seal which is appropriately resistant to the ingress of fluid. The interface between the over-molded form 66 and RF cable 68 is appropriately resistant to the ingress of fluid due to a chemical PVC-to-PVC or other fluid-tight seal provided therebetween.

The RF cable 68 connects the output of tuning and matching circuitry to the MRI system preamplifier. Preferably, the cable 68 has been constructed from a non-magnetic version of a standard RG174 cable. Over the outer cable insulation, a non-toxic PVC outer jacket has been molded. The PVC jacket provides an appropriate non-toxic contact with a patient and also provides an electrical field insulating distance between the patient and the outer electrical shield of the cable thereby preventing the risk of RF burn.

In the preferred embodiment, a printed circuit board 70 including the tuning circuitry is disposed adjacent a distal end of the insert portion 60. The circuit board 70 is disposed below the surface of the Delrin™ plastic such that it is not exposed to the patient or to sterilants. Similarly, a second printed circuit board 72 carrying a matching circuit, and detuning circuitry for protection during RF excitation and, preferably a preamplifier, is disposed adjacent a proximal end of the insert portion 60 adjacent a juncture of the shaft portion 62 and the insert portion 60. The second circuit board 72 is also preferably imbedded below the plastic surface.

In order to create an accurate frame of reference for imaging, the vaginal fascia probe 30 is held stationary relative to the imaged tissue during the imaging sequence. Preferably, the probe 30 is secured by a clamp 74, which grips the over-molded form 66. Preferably, the probe is clamped into its stationary position after it has been inserted into the vaginal cavity of the patient, to accommodate the comfort of the patient as much as possible.

Figure 3A:
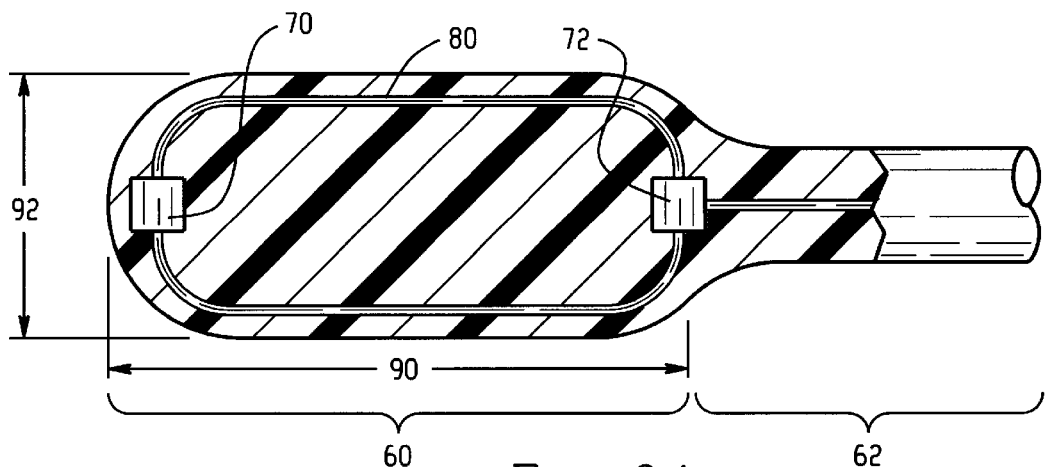
FIG. 3A is a top view of the vaginal cavity probe in partial section.
Figure 3B:
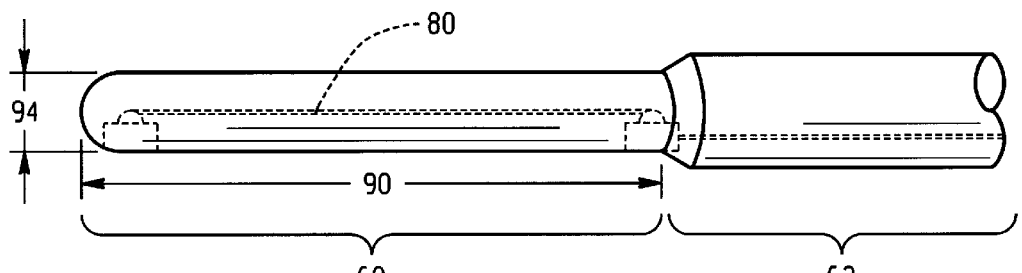
FIG. 3B is a side expanded view of the vaginal cavity probe.

With reference to FIGS. 3A and 3B, with continuing reference to FIG. 2, the insert portion 60 of the RF coil assembly preferably has a coil loop 80 embedded in the probe. The RF coil loop 80 senses resonance signals of relaxing dipoles during an imaging sequence. The coil loop 80 is connected at the distal end with the tuning circuit 70 and at the proximal end with the matching circuit 72. The lead 68 is connected to the coil loop via the matching circuit 72. In one embodiment, the coil loop 80, the tuning circuit 70, and the matching circuit are molded into a unitary medical grade plastic insert and shaft unit.

Figure 4:
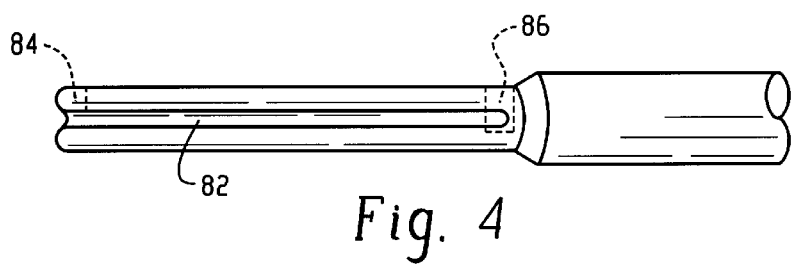
FIG. 4 is a side view of a notched embodiment.

In the embodiment of FIG. 4, a groove 82 is cut or otherwise formed into a periphery of the insert 60 to receive the coil loop 80. A recess or notch 84 receives the tuning circuit and another recess or pocket 86 receives the matching circuit A medical grade epoxy is applied to the whole of the insert portion 60 and preferably, to the shaft portion 62 at least back to the over-molded form 66. The application of the epoxy insures that the RF coil loop 80 is secured within the groove 82. Additionally, the epoxy provides an easily sterilizable, smooth surface to facilitate multiple uses of the coil assembly.

The preferred usage of the coil assembly is to examine the anatomical vicinity of the female urethra. Preferably, as is illustrated in FIGS. 3A and 3B, the insert portion 60 has a length parallel to the shaft portion 62 of nominally 80 mm and preferably not less than 60 mm. If the coil 80 is too short in this dimension, it will not receive resonance signals from the entire area of interest. Also, this dimension is preferably no greater than 100 mm. As the length of the coil 82 increases, the signal to noise ratio decreases, and as a result image quality degrades.

A width 92, perpendicular to the length 90, is preferably 35 mm. If the width 92 is too short, the whole anatomy of interest is not imaged. Preferably, the width 92 is no less than 25 mm. The width 92 is limited by physical restraints of the vaginal cavity. As the width increases, so does patient discomfort and tissue compression. This, of course, varies from patient to patient, but in order to accommodate most patients, the width 92 is preferably no greater than 42 mm.

A height 94 is preferably 10 mm. Any added height stretches the vaginal cavity in an unwanted direction, distorting the tissues of interest, providing degraded image quality. On the other hand, any less height, and the insert portion 60 becomes more knife-like. Narrow or sharp edges increase patient discomfort and risk patient injury.

Moreover, the insert portion 60 is thick enough to remain rigid under stresses that result from being inserted into the vaginal cavity. The more stationary the coil, the more assurance will be had that the region of interest remains still during imaging.

Figure 5:
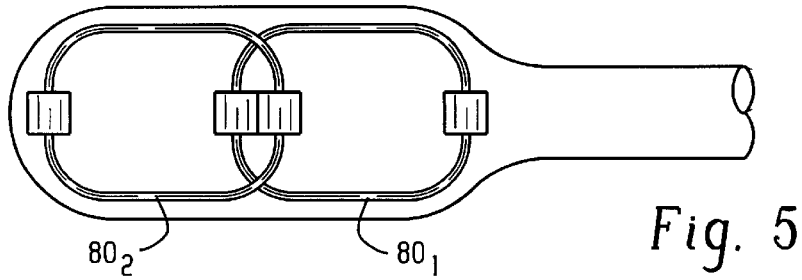
FIG. 5 is an alternate embodiment utilizing two loop coils.

With reference to FIG. 5, in an alternate embodiment, multiple coil loops are utilized instead of a single coil loop. For example, instead of a single coil with a length of 80 mm in length, two coils $80_1$ and $80_2$ measuring just over 40 mm in length are utilized. Beneficially, the signal to noise ratio of each individual coil is increased, at the cost of extra tuning and matching circuitry. Other coil array patterns including quadrature coil arrays are also contemplated.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A magnetic resonance apparatus comprising:
    a main magnet assembly for producing a substantially uniform main magnetic field through an imaging region;
    an RF transmit coil assembly for exciting and manipulating magnetic resonance in selected dipoles of a subject in the imaging region;
    an RF vaginal coil assembly for insertion into a vaginal cavity of the subject and reception of magnetic resonance signals from tissues adjacent the vaginal cavity, the coil assembly including:
    at least one coil loop at a distal end of a head of the assembly, relative to a shaft of the assembly; and,
    a tuning circuit mounted on the head connected directly with the coil loop at the distal end of the head;
    a reconstruction processor for reconstructing the received magnetic resonance signals.

2. The magnetic resonance apparatus as set forth in claim 1, wherein the RF vaginal coil assembly includes:
    a medical grade plastic member having an insert portion and a shaft portion, the shaft portion defining a longitudinal axis of the RF receive coil assembly.

3. The magnetic resonance apparatus as set forth in claim 2, wherein the insert portion includes:
    a head having a length parallel to the longitudinal axis which is longer than a width transverse to the longitudinal axis.

4. The magnetic resonance apparatus as set forth in claim 3, wherein the length is greater than 60 mm and less than 100 mm.

5. The magnetic resonance apparatus as set forth in claim 4, wherein the length is 80 mm.

6. The magnetic resonance apparatus as set forth in claim 3, wherein the width is greater than 25 mm and less than 42 mm.

7. The magnetic resonance apparatus as set forth in claim 6, wherein the width is 35 mm.

8. The magnetic resonance apparatus as set forth in claim 3, further including:
    a thickness that is about 10 mm.

9. The magnetic resonance apparatus as set forth in claim 3, further including:
    a groove defined in a periphery of the head extending from the shaft portion, to a distal end, and back to the shaft portion.

10. The magnetic resonance apparatus as set forth in claim 1, further including:
    a second coil loop mounted on the head adjacent a proximal end of the head having an area defined by a perimeter of the second coil loop, which area partially overlaps an area defined by a perimeter of the at least one coil loop.

11. A magnetic resonance apparatus comprising:
    a main magnet assembly which produces a main magnetic field through an imaging region;
    an RF transmit coil assembly for exciting and manipulating magnetic resonance in selected dipoles of a subject in the imaging region;
    an RF vaginal coil assembly including a shaft portion and a head portion, the head portion being elongated relative to a length parallel to a longitudinal axis of the vaginal coil assembly, which length is longer than a width transverse to the longitudinal axis;
    a groove defined inward in an outermost peripheral edge of the head, the groove extending from the shaft portion, to a distal end, and back to the shaft portion;
    at least one RF coil loop disposed within the outermost peripheral groove;
    a reconstruction processor for reconstructing the received magnetic resonance signals.

12. The magnetic resonance apparatus as set forth in claim 11, further including:
    tuning circuitry connected with the coil loop adjacent the distal end of the head;
    matching circuitry connected with the coil loop adjacent a juncture of the shaft portion and the insert portion.

13. The magnetic resonance apparatus as set forth in claim 12, further including:
    a coating of medical grade epoxy over at least the insert portion to seal crevices and to secure the RF coil loop in the groove.

14. A magnetic resonance method comprising:
    inducing a main magnetic field in a pelvic region of a female subject;
    inserting a vaginal receive coil probe into a vaginal cavity of the subject, the vaginal receive coil probe having an insert portion, a shaft portion, and a coil loop, the coil loop circumscribing and defining an outermost periphery of the insert portion;
    exciting and manipulating magnetic resonance in selected dipoles of vaginal fascia tissue surrounding the vaginal cavity;
    receiving magnetic resonance signals from the vaginal fascia tissue with the vaginal receive coil probe;
    demodulating and reconstructing the magnetic resonance signals into an image representation.

15. The method as set forth in claim 14, wherein the step of inserting a vaginal coil probe includes:
    inserting an insert portion of the receive coil into the vaginal cavity, the insert portion having three orthogonal dimensions, the first dimension being greater than 60 mm and less than 100 mm, and the second dimension being greater than 25 mm and less than 42 mm.

16. The method as set forth in claim 15, wherein the first dimension is 80 mm, the second dimension is 35 mm and the third dimension is 10 mm.

17. A magnetic resonance vaginal insert probe for receiving magnetic resonance signals from vaginal tissue, the probe comprising:

a shaft portion;

an insert portion connected at a proximal end with the shaft portion, the insert portion including:

a medical grade polymer head of 60–100 mm in length, 25–42 mm in width and 8–12 mm in thickness, at least one coil loop encased in and extending around an outermost periphery of the medical grade polymer head.

18. The probe as set forth in claim 17, wherein:

a distal end of the head is smoothly rounded in both width and thickness directions.

19. A magnetic resonance vaginal insert probe comprising:

a shaft portion connected with a medical grade polymer head;

at least one coil loop encased in and extending around a periphery of the medical grade polymer head;

a tuning circuit encased in the head adjacent a distal end, the tuning circuit being connected with the coil loop to adjust its resonance frequency;

a matching circuit encased in the head or the shaft portion adjacent the insert portion proximal end; and an RF output cable connected with the matching circuit and extending through the shaft portion.

20. The probe as set forth in claim 19, wherein the head is substantially:

80 mm in length, 35 mm in width, and, 10 mm in thickness.

21. A magnetic resonance probe comprising:

a shaft portion;

an insert portion connected at a proximal end with the shaft portion, the insert portion including:

a medical grade polymer head, at least one coil loop extending around an outside groove of the medical grade polymer head; and, a medical grade epoxy layer sealing the coil loop into the groove of the head, the epoxy layer defining an interfacing surface with the surrounding tissue.

* * * * *